United States Patent [19]

Kabeta

[11] Patent Number: 4,814,473

[45] Date of Patent: Mar. 21, 1989

[54] PROCESS FOR PRODUCING 5-VINYLBICYCLO[2.2.1]HEPTYLTRI-CHLOROSILANE

[75] Inventor: Keiji Kabeta, Ohta, Japan

[73] Assignee: Toshiba Silicone Co., Ltd., Japan

[21] Appl. No.: 246,230

[22] Filed: Sep. 19, 1988

[30] Foreign Application Priority Data

Oct. 7, 1987 [JP] Japan ................... 62-253396

[51] Int. Cl.$^4$ .............................................. C07F 7/08
[52] U.S. Cl. .................................................. 556/479
[58] Field of Search ........................................ 556/479

[56] References Cited

U.S. PATENT DOCUMENTS 4,100,172  7/1978  Mui et al. ..................... 556/479 X
4,417,068  11/1983  Kollmeier et al. ................. 556/479
4,579,965  4/1986  Kanner et al. ..................... 556/479
4,640,968  2/1987  Watanabe et al. ............... 556/479 X
4,642,356  2/1987  Langner et al. ................. 556/479 X
4,722,975  2/1988  Itoh et al. ............................. 525/288

OTHER PUBLICATIONS

The Merck Index: Tenth Edition; see 7319 and 7320, p. 1073.

*Primary Examiner*—Paul F. Shaver

[57] ABSTRACT

In a process for producing 5-vinylbicyclo[2.2.1]heptyltrichlorosilane by addition-reacting 5-vinylbicyclo[2.2.1]hepta-2-ene with trichlorosilane, a process for producing 5-vinylbicyclo[2.2.1]heptyltrichlorosilane characterized in that a palladium metal or palladium complex is used as a catalyst.

3 Claims, No Drawings

PROCESS FOR PRODUCING 5-VINYLBICYCLO[2.2.1]HEPTYLTRICHLOROSILANE

The present application claims the priority of Japanese patent application Ser. No. 62-253396 filed on Oct. 7, 1987.

BACKGROUND OF THE INVENTION

The present invention relates to a process for producing 5-vinylbicyclo[2.2.1]heptyltrichlorosilane which is useful as a copolymerizable monomer or modifier, etc. for organic high molecular weight compounds.

5-vinylbicyclo[2.2.1]heptyltrichlorosilane is produced by subjecting 5-vinylbicyclo[2.2.1]hepta-2-ene (II) and trichlorosilane (III) to an addition reaction (hydrosilylation) in the presence of a chloroplatinic acid catalyst [J. Gen. Chem. USSR, 31 [4], 1109–1117 (1961)].

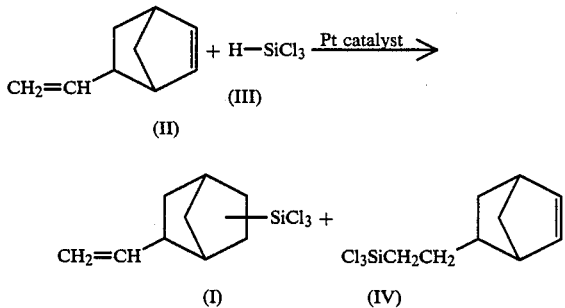

According to this process, 5-vinylbicyclo[2.2.1]heptyltrichlorosilane (I), which the addition occurs on the double bond present in the ring of the cyclic hydrocarbon, and 5-(2-trichlorosilylethyl)bicyclo-[2.2.1]hepta-2-ene (IV), which is obtained by reacting with the vinyl group outside the ring, are produced in almost equimolar amounts. In addition, the reaction yield is also as low as 35.8%. The hydrosilylation using chloroplatinic acid as the catalyst involves a significant drawback that the reaction 10 selectivity of obtaining compound (I) alone is low. Further, (I) and (IV) are structural isomers in which only the position to be added is different and, it is impossible to isolate (I) alone by distillation.

A known method for enhancing the selectivity uses trimethoxysilane instead of trichlorosilane (U.S. Pat. No. 4,100,172).

This method is characterized in that the vinyl group outside the ring is predominantly reacted with trimethoxysilane in the presence of an addition catalyst (chloroplatinic acid) to selectively give 5-(2-trimethoxysilylethyl)bicyclo[2.2.1]hepta-2-ene. However, this method is not suited for obtaining the compound having a vinyl group outside the ring which is the object of the present invention.

In the present invention, the reason why the compound having a carbon-carbon double bond at the carbon terminal such as a vinyl group and containing a reactive silyl group is necessary is because it is wished to produce a compound having a high reactivity as a modifier for organic high molecular substances and to produce a raw material having a great effect of quality modification. Namely, the carbon-carbon double bond generally shows a higher reactivity when it is present at the carbon terminal than when it is present within the ring of the cyclic hydrocarbon. For example, where a mixture of polymerizable monomers containing an alkenyl group such as ethylene, propylene, (meth)acrylic acids or (meth)acrylic acid esters, etc. and the compound described above are copolymerized with each other using a radical generator such as an organic peroxide, copolymers tend to be produced in which intake of compound (I) is larger than when the compound of formula (IV) having the double bond within the ring and the compound (I) having the vinyl group outside the ring are both present. From this tendency, a process for selectively producing the compound (I) of the present invention having a vinyl group outside the ring in a high yield has been strongly desired in view of molecular design of high molecular substances.

SUMMARY OF THE INVENTION

An object of the present invention is to provide novel a process for selectively producing an organic silicon compound having outside the ring an aliphatic unsaturated group such as a vinyl group by hydrosilylation utilizing the difference in reactivity of double bonds present in the ring and outside the ring of the cyclic hydrocarbon. In particular, an object of the present invention is to provide a process for producing the cyclic hydrocarbon group-containing silane having an alkenyl group having a high polymerization reactivity outside the ring easily in a high yield, by selecting the most appropriate catalyst which causes the hydrosilylation to predominantly react between the double bond in the ring and hydrosilane.

As a result of extensive investigations of a method for hydrosilylation of the double bond within 5-vinylbicyclo[2.2.1]-hepta-2-ene, the present inventors have found that by the use of a palladium catalyst, trichlorosilane is predominantly added to the double bond within the ring and have come to accomplish the present invention.

The present invention is a process for producing 5-vinylbicyclo[2.2.1]heptyltrichlorosilane characterized in that in addition-reaction of 5-vinylbicyclo-[2.2.1]hepta-2-ene and trichlorosilane to produce 5-vinylbicyclo[2.2.1]heptyltrichlorosilane, palladium metal or a palladium complex is used as the catalyst.

The palladium catalyst used in the present invention can be selected from any of the group consisting of palladium metal, a zero valent palladium complex and a bivalent palladium complex. Examples of these catalysts include metals such as palladium deposited on carbon, preferably charcoal; zero valent complexes such as tetrakis(triphenylphosphine) palladium (0), carbonyltris(triphenylphosphine) palladium (0), (η-ethylene)-tris(triphenylphosphine) palladium (0), bis(η-ethylene)-bis(triphenylphosphine) palladium (0), etc.; bivalent complexes such as dichlorobis(triphenyl-phosphine) palladium (II), dichlorobis(triethylphosphine) palladium (II), dichlorobis(diphenylphosphino)ethane palladium (II), dichlorobis(benzonitrile) palladium (II), dibromobis-(benzonitrile) palladium (II), dichlorobis-(acetonitrile) palladium (II), dichloro(1,5-cyclooctadiene) palladium (II), dichlorobis(η-allyl) palladium (II), bis(acetylacetonate) palladium (II), palladium dichloride, etc. Of these catalysts, preferred are tetrakis(triphenylphosphine) palladium, carbonyltris(triphenylphosphine) palladium, (η-ethylene)tris(triphenyl-phosphine) palladium, dichlorobis(triphenylphosphine) palladium, dichlorobis(triethylphosphine) palladium, etc.

It is preferred that the amount of palladium catalyst present in the reaction system be 0.001 to 5.0 parts by weight, more preferably 0.01 to 1.0 parts by weight, based on 100 parts by weight of 5-vinylbicyclo[2.2.1-]hepta-2-ene. If the amount of the catalyst present is less than 0.001 parts by weight, the reaction rate is not sufficient. When the amount of the catalyst present exceeds 5.0 parts by weight, the reaction rate is not improved further and is not preferred from an economical viewpoint.

It is preferred that a molar ratio of trichlorosilane charged be in a range of 0.8 to 1.3 based on 5-vinylbicyclo[2.2.1]heptyltrichlorosilane but this preferred molar ratio is not critical. The hydrosilylation reaction can be generally performed at a temperature in the range of from 20° C. to 150° C., and preferably in a range of 90° C. to 110° C. The reaction is usually carried out under ordinary atmospheric pressure; but, if necessary and desired, the reaction may be carried out under a higher pressure or under reduced pressure. A solvent is not necessary as a medium for the reaction but may be used to enhance solubility of the catalyst or control the temperature. As such a solvent, there may be used any solvent having no reactive with chlorosilane. Examples include hydrocarbon solvents such as toluene, xylene, cyclohexane, n-hexane, n-heptane, naphtha, mineral spirit, petroleum benzine, etc.; halogenated hydrocarbon solvents such as carbon tetrachloride, trichloroethylene, perchloroethylene, 1,1,1-trichloroethylene, etc.; ethereal solvents such as ethyl ether, tetrahydrofuran, ethylene glycol diethyl ether, etc.; ester solvents such as ethyl acetate, butyl acetate, amyl acetate, etc.; ketonic solvents such as acetone, methyl ethyl ketone, methyl isobutyl ketone, etc. and non-protonic polar solvents such as dimethylformamide, dimethylacetamide, etc.

The reaction time may vary depending upon the catalyst or solvent used, reaction temperature, etc. and is not particularly limited. In general, however, the conditions are set to complete the reaction in 0.5 to 6 hours. The reaction is conducted in a conventional manner. For example, while stirring a mixture of 5-vinylbicyclo [2.2.1]hepta-2-ene and the palladium catalyst, the mixture is heated to a predetermined temperature and trichlorosilane is added dropwise to the heated mixture. The compound obtained can be easily purified by distillation because the compound is obtained by the reaction with a high selectivity. In order to increase thermal stability of the obtained compound, distillation may be carried out after a known appropriate antioxidant incorporated; or, a suitable amount of the antioxidant may be added to the obtained compound during purification, etc. since these operations are conventional.

The process of the present invention as described above provides an excellent reaction selectivity as a result of the catalyst used. The catalyst used in the process of the present invention has a specificity to allow trichlorosilane to predominantly add to the double bond within the ring as opposed to adding to both the double bonds within the ring and outside the ring of the cyclic hydrocarbon. Therefore, 5-vinylbicyclo[2.2.1]heptyltrichlorosilane having the double bond outside the ring can be obtained in a high yield and high purity. Such an organic silicon compound possesses the vinyl group having a high reactivity outside the ring and is thus extremely useful as a raw material for various reactions and as an intermediate, etc., in molecular design. For example, when this organic silicon compound is copolymerized with polymerizable monomer having other alkenyl group using organic peroxides, etc., copolymers can easily be obtained. In addition, there is the additional effect in that the copolymers contain the reactive silyl group and therefore, can be also crosslinked through the silyl group.

The organic silicon compound thus obtained in the process of the present invention is widely applicable to various fields as a raw material for synthesis of polyorganosiloxanes, silane-modified organic polymers and an intermediate thereof, or utilization for crosslinking between organic polymers, etc.

EXAMPLES

The present invention is now described in more detail by referring to the examples but is not deemed to be limited only to these examples. Parts are all by weight, unless otherwise indicated.

EXAMPLE 1

To a four-necked flask equipped with a refluxing condenser, a thermometer, a dropping funnel and a stirrer were charged 120 parts (0.1 mol) of 5-vinylbicyclo[2.2.1]hepta-2-ene and 0.1 part of dichlorobis(triphenylphosphine) palladium. While stirring, the mixture was heated to 90° C. To the solution mixture, was dropwise added 150 parts (1.1 mol) of trichlorosilane over 3 hours. Then, the mixture was heated at 90° C. for a further 2 hours while stirring to complete the reaction. The obtained reaction mixture was distilled under reduced pressure (4 mmHg) to give 228 parts of a colorless transparent fraction showing a boiling point of 85° to 87° C. With respect to this fraction, a refractive index, specific gravity, IR and NMR were measured. The results are shown below.

Refractive index: $n_D^{25}$ 1.5080
Specific gravity: $d_4^{25}$ 1.229
IR (liquid film method): 3070 cm$^{-1}$ ($\nu$CH of double bond), 2950, 2860 cm$^{-1}$ (aliphatic $\nu$CH), 1635 cm$^{-1}$ ($\nu$C=C), 990, 910 cm$^{-1}$ ($\delta$CH of double bond)
NMR: (90 MHz, solvent, CCl$_4$; internal standard, TMS) 0.95–3.00 ppm (m, 10H, aliphatic proton) 5.00–5.10 ppm (m, 2H, proton of vinyl group) 5.95–6.10 ppm (m, 1H, proton of vinyl group)

From the foregoing results, it was confirmed that the obtained fraction was 5-vinylbicyclo[2.2.1]heptyltrichloro-silane. It was also confirmed that the yield was as high as 89% and the purity was high.

Comparative Example 1

It was attempted to produce 5-vinylbicyclo[2.2.1-]heptyltrichlorosilane in a manner similar to Example 1 except that 0.1 part of dichlorobis(triphenylphosphine) platinum was used in place of dichlorobis(triphenylphosphine) palladium. However, it was noted from NMR that the product was impure, namely, 5-(2-trimethoxysilylethyl)bicyclo[2.2.1]hepta-2-ene was contained in large quantities. It was impossible to isolate 5-vinylbicyclo[2.2.1]heptyltrichlorosilane.

While the invention has been described in detail and with reference to specific embodiments thereof, it is apparent to one skilled in the art that various changes and modifications can be made therein without departing from the spirit and the scope of the present invention.

What is claimed is:
1. In a process for producing 5-vinylbicyclo[2.2.1-]heptyltrichlorosilane by addition-reacting 5-vinylbicy- clo[2.2.1]hepta-2-ene with trichlorosilane, a process for producing 5-vinylbicyclo[2.2.1]heptyltrichlorosilane characterized in that a palladium metal or palladium complex is used as a catalyst.

2. A process as claimed in claim 1, wherein said catalyst is used in a range of 0.001 to 5.0 parts by weight based on 100 parts by weight of 5-vinylbicyclo[2.2.1]hepta-2-ene.

3. A process as claimed in claim 2, wherein said catalyst is used in a range of 0.01 to 1.0 parts by weight based on 100 parts by weight of 5-vinylbicyclo[2.2.1]hepta-2-ene.

* * * * *